(12) United States Patent
Tao et al.

(10) Patent No.: US 9,360,428 B2
(45) Date of Patent: Jun. 7, 2016

(54) INTERFEROMETRIC FOCUSING OF GUIDE-STARS FOR DIRECT WAVEFRONT SENSING

(71) Applicant: The Regents of the University of California, Oakland, CA (US)

(72) Inventors: Xiaodong Tao, Santa Cruz, CA (US); Joel A. Kubby, Bonny Doon, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/769,893

(22) PCT Filed: Mar. 14, 2014

(86) PCT No.: PCT/US2014/027680
§ 371 (c)(1),
(2) Date: Aug. 24, 2015

(87) PCT Pub. No.: WO2014/152739
PCT Pub. Date: Sep. 25, 2014

(65) Prior Publication Data
US 2016/0003740 A1    Jan. 7, 2016

(51) Int. Cl.
*G01N 21/45* (2006.01)
*G01N 21/64* (2006.01)
*G01N 21/49* (2006.01)
*G02B 21/16* (2006.01)
*G02B 21/24* (2006.01)
*G02B 21/36* (2006.01)
*G01N 21/47* (2006.01)

(52) U.S. Cl.
CPC ............ *G01N 21/6458* (2013.01); *G01N 21/45* (2013.01); *G01N 21/49* (2013.01); *G02B 21/16* (2013.01); *G02B 21/244* (2013.01); *G02B 21/245* (2013.01); *G02B 21/365* (2013.01); *G01N 2021/4709* (2013.01); *G01N 2201/0675* (2013.01)

(58) Field of Classification Search
CPC ............. G01J 9/02; G01B 9/02; G01N 21/45; G01N 21/6456
See application file for complete search history.

(56) References Cited

U.S. PATENT DOCUMENTS

| | | | |
|---|---|---|---|
| 8,866,107 B2 * | 10/2014 | Cui | ........................ G01N 21/49 |
| | | | 250/252.1 |
| 2004/0227101 A1 | 11/2004 | Iketaki | |
| 2006/0033933 A1 | 2/2006 | Feierabend | |
| 2009/0137990 A1 | 5/2009 | Sheinis | |
| 2010/0105105 A1 | 4/2010 | Azucena | |
| 2013/0015367 A1 | 1/2013 | Cui | |

* cited by examiner

*Primary Examiner* — David Porta
*Assistant Examiner* — Faye Boosalis
(74) *Attorney, Agent, or Firm* — Lumen Patent Firm

(57) ABSTRACT

Interferometric focusing (IF), rather than conventional geometric focusing, of excitation light onto a guide-star that is embedded deeply in tissue, increases its fluorescence intensity. The method can extend the depth of wavefront measurement and improve correction inside of tissues because of its ability to suppress both scattering of diffuse light and aberration of ballistic light. The results showed more than two times improvement in SNR and RMS error of the wavefront measurement. Although only ballistic light in the excitation path is corrected, the intensity after wavefront correction increased by 1.5 times. When applying IF to a two-photon microscope with a near infra-red laser, this method would further extend the measurement depth and achieve high SNR for the wavefront sensor.

5 Claims, 14 Drawing Sheets

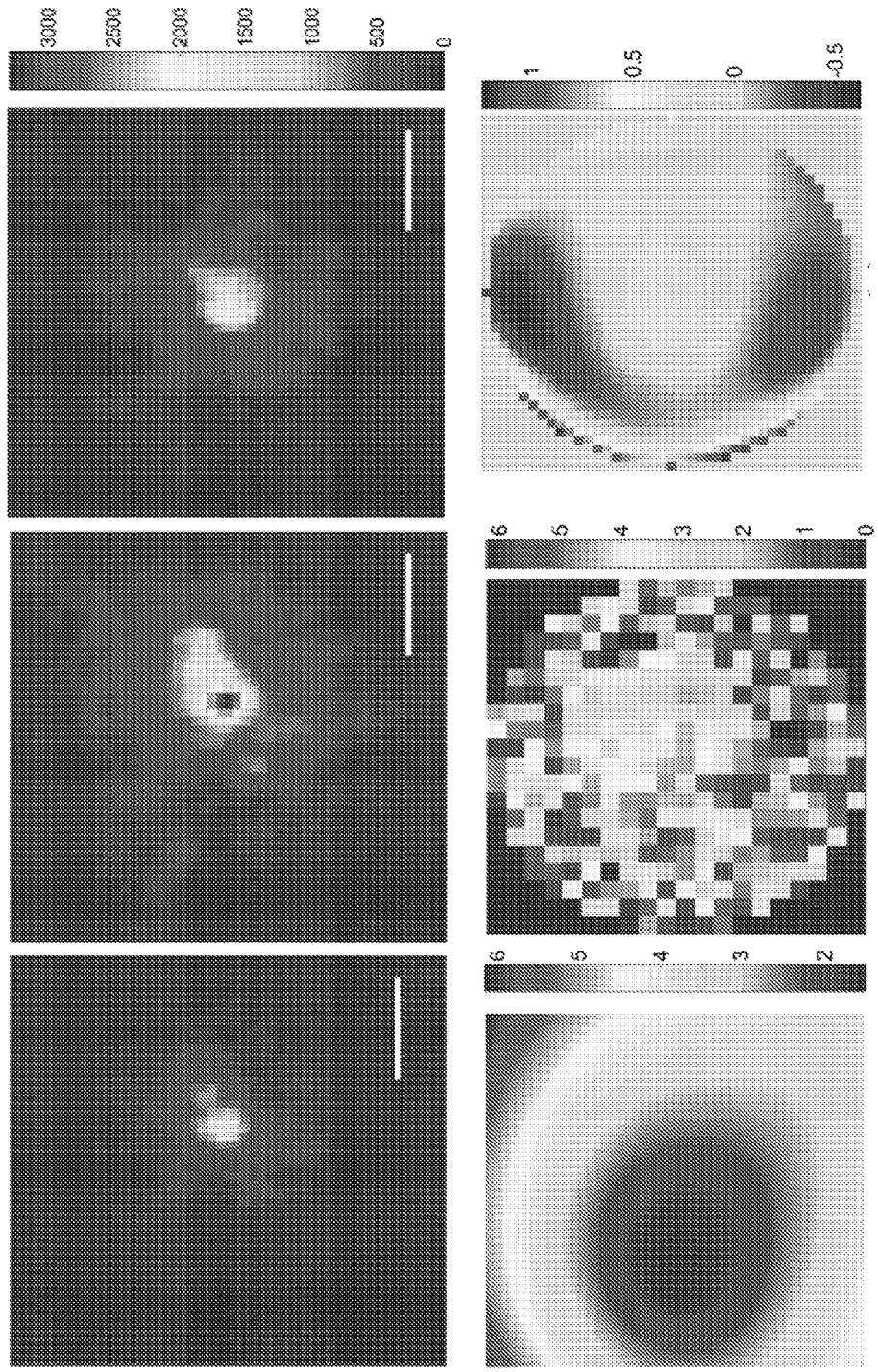

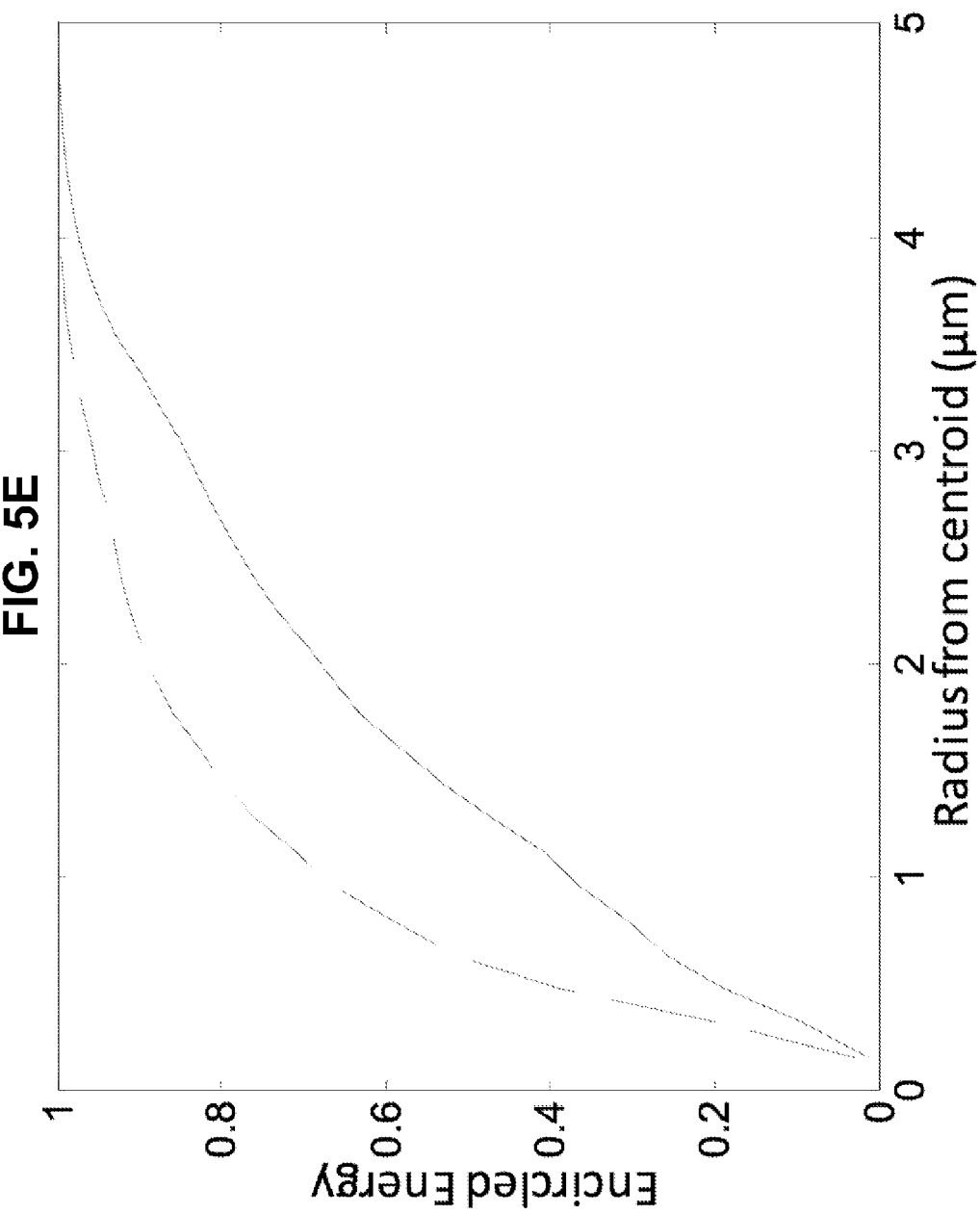

FIG. 6A
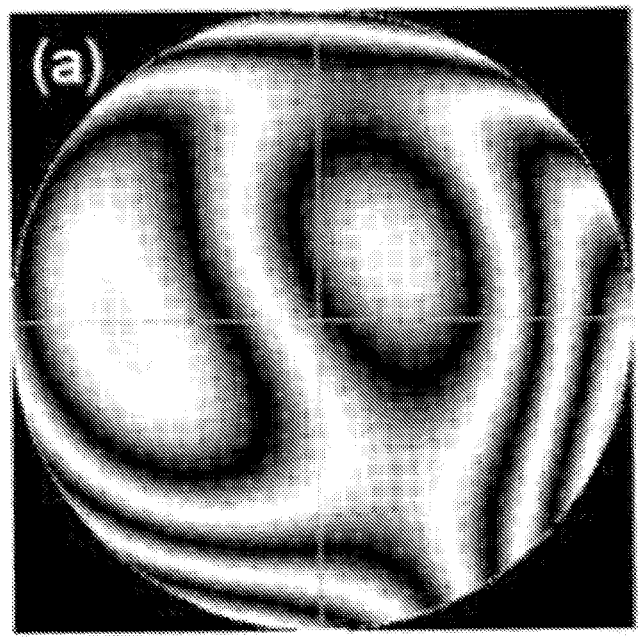
FIG. 6B
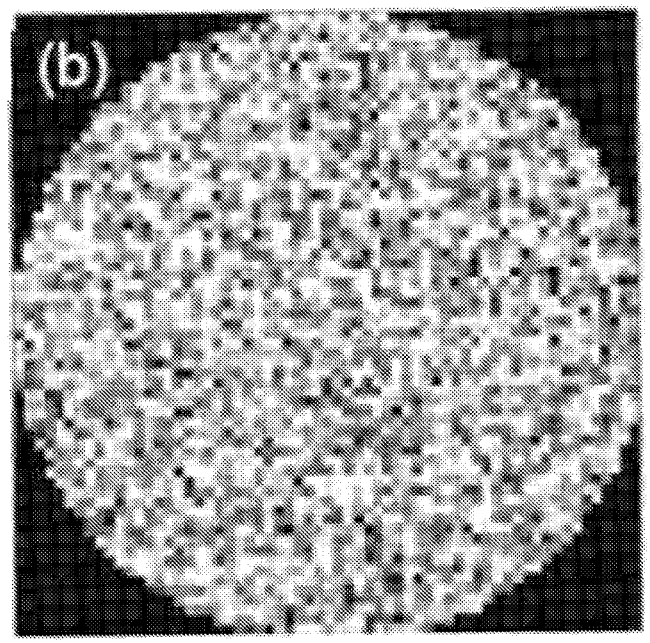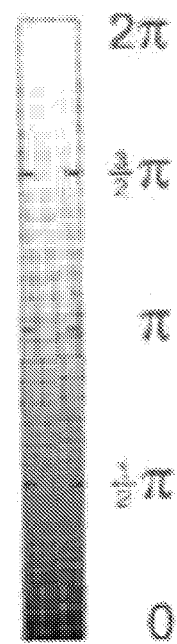

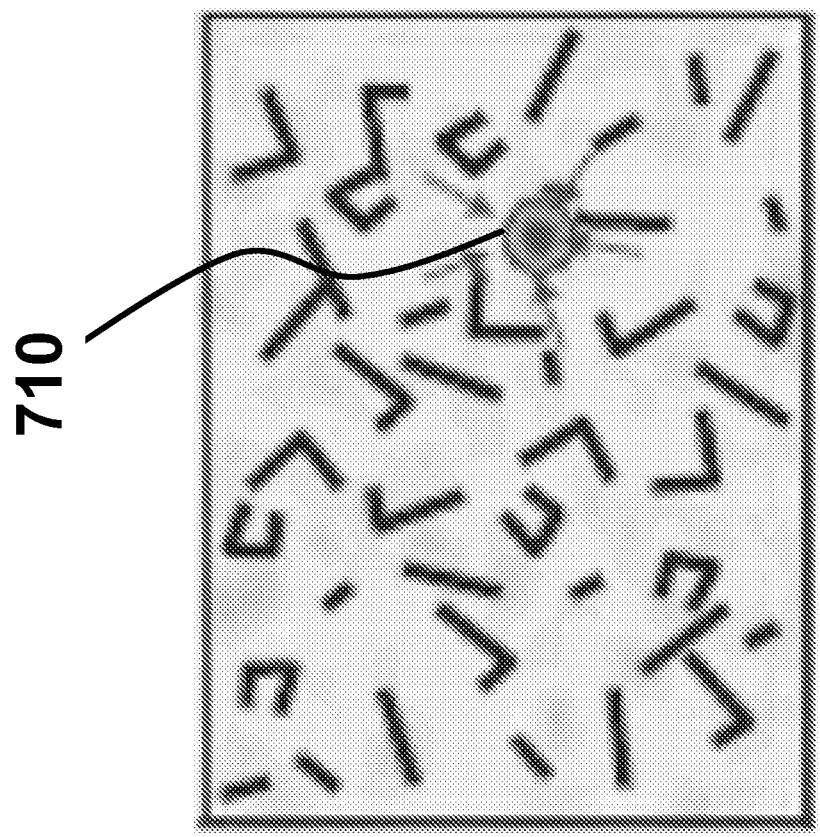
FIG. 7B

US 9,360,428 B2

INTERFEROMETRIC FOCUSING OF GUIDE-STARS FOR DIRECT WAVEFRONT SENSING

CROSS-REFERENCE TO RELATED APPLICATIONS

This application is a 371 of PCT application PCT/US2014/027680 filed on Mar. 14, 2014. PCT/US2014/027680 filed on Mar. 14, 2014 claims the benefit of U.S. Provisional application 61/781,022 filed on Mar. 14, 2013.

FIELD OF THE INVENTION

This invention relates to methods and systems for noninvasive imaging of biological tissues at a subcellular level.

BACKGROUND OF THE INVENTION

With the advantages of high-resolution and viewing of live organisms, optical microscopy has become an important tool for biological research and continues to open new avenues in its capabilities. In recent years, image resolution and speed has been dramatically improved. However, the improvement of the resolution and penetration depth for optical microscopy is still in its infancy. As light passes through biological tissue, it can be absorbed, refracted and scattered, limiting the resolution and depth of optical imaging in biological tissues. Overcoming these challenges will benefit a wide range of applications from basic biological research to clinical investigations. The present invention addresses these challenges.

SUMMARY OF THE INVENTION

Optical microscopy provides noninvasive imaging of biological tissues at subcellular level. The optical aberrations induced by the inhomogeneous refractive index of biological samples limits the resolution and can decrease the penetration depth. To compensate refractive aberrations, adaptive optics with Shack-Hartmann wavefront sensing has been used in microscopes. Wavefront measurement requires light from a guide-star inside of the sample. The scattering effect limits the intensity of the guide-star, hence reducing the signal to noise ratio of the wavefront measurement. In one aspect of this invention, we demonstrate the use of interferometric focusing of excitation light onto a guide-star embedded deeply in tissue to increase its fluorescent intensity, thus overcoming the excitation signal loss caused by scattering. With interferometric focusing, we more than doubled the signal to noise ratio of the laser guide-star through scattering tissue as well as potentially extend the imaging depth through using AO microscopy.

In another aspect of this invention, an optical microscopy method for noninvasive imaging of a biological tissue is provided. The method uses a combined approach of interferometric wavefront shaping with geometric wavefront shaping. Geometric focusing results in the formation of an image of an object, whereas interferometric focusing results in an increased intensity of light at the focal point, but does not map light from an object to an image. In this aspect, wavefront shaping using interferometric focusing compensates for light scattering. Interferometric focusing focuses light onto a guide-star in a biological tissue to illuminate the guide-star. The fluorescence from the illuminated guide-star is measured using direct wavefront sensing. Wavefront shaping using geometric focusing based on the measured fluorescence from the guide-star is used to correct for refractive aberrations. The combined interferometric and geometric wavefront shaping can then be used in the optical microscopy method. The method could further include a selection process to select the brightest guide-star from a plurality of guide-stars.

BRIEF DESCRIPTION OF THE DRAWINGS

FIGS. 3A-C show according to an exemplary embodiment of the invention a 1 μm diameter fluorescent bead under a 100 μm thick fixed mouse brain tissue sample used as a guide-star for wavefront measurement. FIG. 3 shows the image of the guide-star after compensation of system aberration (top) and the phase map displayed on the SLM (bottom). FIG. 3B shows the image of the guide-star after IF (top) and the phase map to compensate scattering (bottom). The intensity increases more than two times. FIG. 3C shows the image of the guide-star after refractive aberration correction (top) and the phase map measured from a SHWS (bottom). The scale bar is 2 μm.

FIG. 4C shows the SNR improvement 410 of wavefront measurement and intensity improvement 420 for various depths. The error bars represent the standard deviation of the mean.

FIGS. 5A-E show according to an exemplary embodiment of the invention effects of multiple guide-stars. Images of multiple guide-stars before IF (FIG. 5A) and after IF (FIG. 5B). Spot images from the wavefront sensor before IF (FIG. 5C) and after IF (FIG. 5D). Encircled energy of the guide-star before (solid line) and after IF (dashed line) (FIG. 5E). The scale bar is 2 μm.

FIGS. 6A-D show according to an exemplary embodiment of the invention phase patterns for correcting refractive aberrations and wavefront shaping for compensating scattering. FIG. 6A shows phase corrections for refractive image aberrations are typically smooth and continuous over the wavefront corrector. These aberrations have low spatial frequencies and are typically correlated over an "isoplanatic" region that can extend over a ~38 μm diameter patch around the guide-star. FIG. 6B shows wavefront shaping used for "unscattering" light in a turbid sample is typically discontinuous and uncorrelated over the wavefront corrector. The pattern on the SLM has high-spatial frequencies. The scattering compensation extends over a ~10 μm diameter patch around the guide-star. FIG. 6C shows woofer-tweeter speakers in an audio stereo system. The audio signal is filtered by a low-pass and high-pass filter. The low frequencies are passed to the woofer speaker that is designed for producing low-frequency bass notes. The high frequencies are a passed to the tweeter that is designed for producing high frequency treble notes. FIG. 6D shows analogous adaptive optical woofer-tweeter system consisting of a low-order deformable mirror for correction of low-spatial frequency aberrations and a high-order tweeter for correction of high-spatial frequencies. The intervening optics relay an image of the pupil from the woofer to the tweeter.

FIGS. 7A-C show according to an exemplary embodiment of the invention a comparison of conventional geometric focusing of light into highly scattering sample (FIG. 7A) with interferometric refocusing of light onto a fluorescent bead "guide-star" embedded within the sample (FIG. 7B). Most of the light is scattered before reaching the fluorescent bead using geometric focusing. Interferometric refocusing is able to overcome the losses due to scattering by causing multiple beams to constructively interfere at the guide-star. FIG. 7C shows an experimental setup for interferometric refocusing. A laser (532 nm) is expanded by a 30× beam expander and modulated with a spatial light modulator (SLM). A 1:2 demagnifying telescope images the SLM on to the back aperture of a 63× microscope objective. The objective focuses the light on to a sample that is mounted on a XYZ piezo positioning stage. A dichroic mirror (DM) and a bandpass filter (F) block the excitation light. The fluorescent emission is imaged on to an electron multiplying CCD camera (EM-CCD). D, iris diaphragm; PBS, polarizing beam splitter cube; L 1, L 2, L 3, lenses with a focal distance of 200 mm, 100 mm and 150 mm, respectively.

DETAILED DESCRIPTION

Section 1

Figure 1:
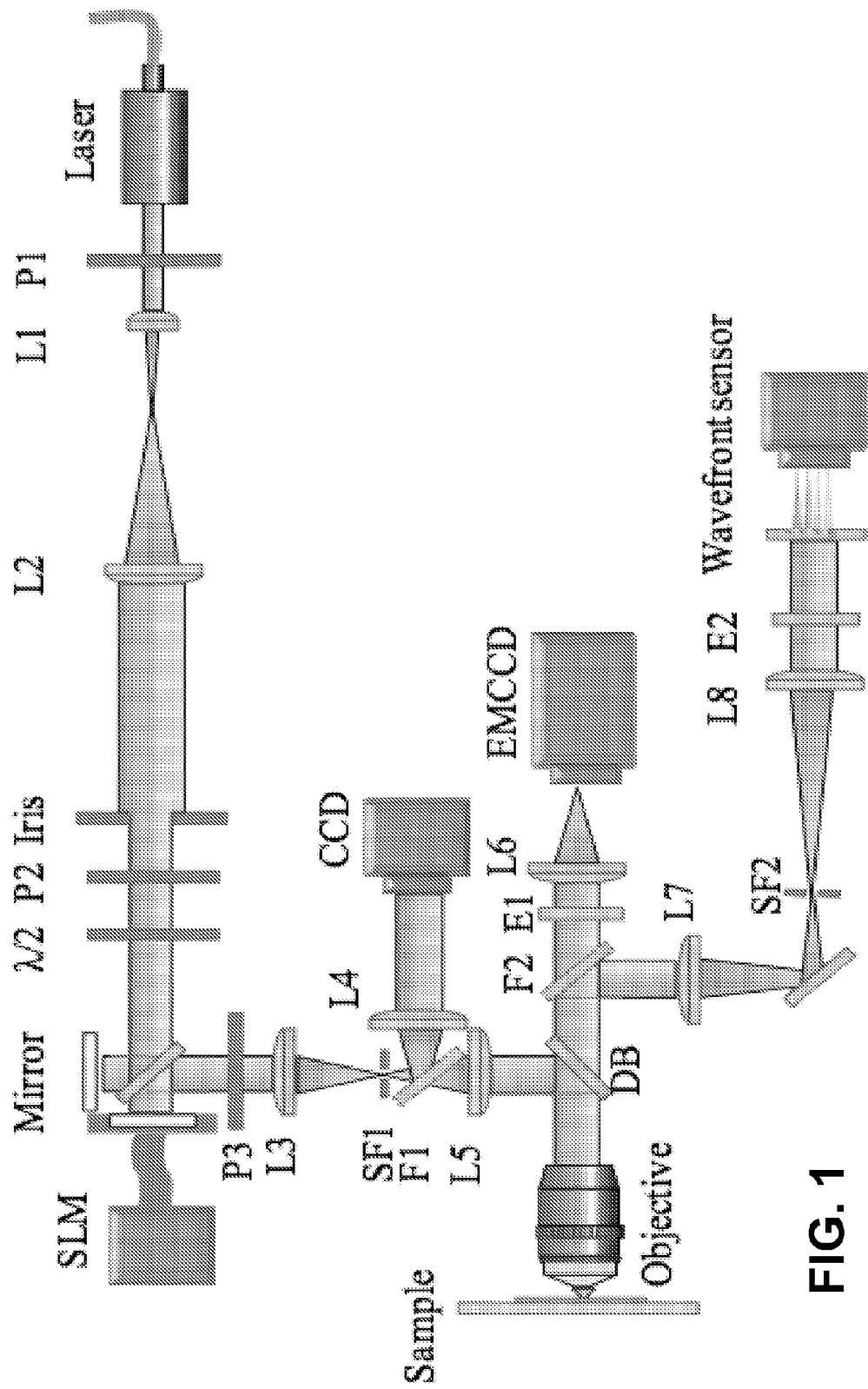
FIG. 1 shows a system layout for using interferometric focusing on to a guide-star according to an exemplary embodiment of the invention. A He—Ne laser emits light at 633 nm for excitation of a fluorescent reference beacon. The laser is modulated by a spatial light modulator (SLM) and generates interferometric focusing at the guide-star by an optimization process using the intensity information from an EMCCD camera. The emission light from the enhanced guide-star feeds into a SH wavefront sensor for direct wavefront measurement. L, lens; F, flipper mirror; P, polarizer; DB, dichroic beamsplitters; E, emission filter; SF, spatial filter.

To correct the refractive aberration, Adaptive Optics (AO) with different strategies has been applied in optical microscopes. The indirect wavefront sensing method was first applied in an AO system to retrieve the optimal phase by maximizing the detected signal from samples. Numerous iterations are required to find the wavefront, causing photobleaching, while limiting the bandwidth of imaging.

The direct wavefront sensing method applies a Shack-Hartmann wavefront sensor (SHWS) or interferometer to measure the wavefront directly using the light from a fluorescent microsphere, fluorescent proteins, or backscattered light from the samples. Other approaches use a direct wavefront measurement based on sequential measurements of the wavefront error in each segment of the aperture, or sequential intensity measurements with different trial aberrations.

In the above methods, the performance relies heavily on the intensity of the ballistic light from the samples. In biological tissues, the ballistic light will be attenuated exponentially with increasing depth because of scattering. When using Shack-Hartmann wavefront sensing, the scattering will not only limit the amount of photons delivered to the guide-star, but also increase the background noise of neighboring guide-stars. Both of these effects reduce the signal to noise ratio (SNR) for wavefront measurements.

Scattering is caused by inhomogeneities in biological tissues. The majority of scattered light from a cell is due to the nucleus and smaller organelles such as mitochondria. The amplitude of elastic scattering loss is noted to be an order of magnitude or more than that of absorption. Although scattering is entirely random, it is a deterministic and time reversible process. The optical phase conjugation (OPC) method has been successfully applied to measure the phase and amplitude of the scattered light field, retrace its trajectory through the scattering medium and recover its original input light field. To measure the light field coming from the observed area, OPC needs coherent light from the area of interest. Meanwhile, ultrasonically encoded focusing has been utilized to generate a guide-star as a coherent point source for phase measurement.

Another method, called interferometric focusing (IF), is also used to estimate the optimal phase of the scattering light field by modulating the phase of illumination light while analyzing the variation of emission light from the sample. By measuring the phase of scattered light from the point source in the sample one can match the scattering behavior of the turbid material and as a result allow constructive interference to occur, thereby increasing intensity at the point source. In conventional focusing the paths of light rays are determined by Fermat's principle of least time; light will take a path between two points that minimizes the travel time. Interferometric focusing uses the coherent properties of light to cause constructive interference at the focus and this is done by adjusting the phase of each scattering channel to obtain constructive interference at the bead.

To increase the speed of the phase estimation, different methods have been applied, such as a genetic algorithm, spatial frequency modulation and parallel wavefront optimization method. Fast light modulators, such as the Digital Micromirror Device (DMD) from Texas Instruments and segmented deformable mirrors from Boston Micromachines, have also been used to further speed up the optimization process.

Although scattering will exponentially reduce the intensity of ballistic light with the imaging increasing depth, correction of refractive aberration still benefits the imaging resolution and contrast. For two-photon imaging of mouse brain tissue, it has been shown that wavefront distortions are the main factor for enlargement and distortion of the point spread function (PSF) at intermediate imaging depths. Wavefront correction can dramatically reduce the surrounding lobes of the PSF in the brain tissues. The advantages of the large isoplanatic angle and fast correction speed make it suitable for live imaging.

The invention demonstrates the use of the IF method, rather than conventional geometric focusing to concentrate excitation light onto a guide-star in tissue for direct wavefront measurement using a SHWS. Interferometric focusing can increase the fluorescent intensity of the guide-star, thus overcoming signal loss caused by scattering. By minimizing scattering, less power is required to generate a guide-star bright enough for wavefront measurement. The wavefront can be measured by a SHWS with fluorescence from the illuminated laser guide-star. These measurements will subsequently be used in our AO microscope to overcome refractive image aberrations using adaptive geometric optics. With the IF of light, we are able to double the illumination of the laser guide-star through scattering tissue and potentially double the thickness of tissue that can be corrected using AO microscopy. In addition, the correction of the refractive aberration when using AO provides a larger correction field, compared to the scattering compensation while using IF.

FIG. 1 shows a configuration of the system using IF. A HeNe laser (LHX1, CVI Melles Griot) was used as the excitation source. The beam was further expanded by lenses L1 and L2, which covers an area with a radius of 4 mm on a reflective spatial light modulator (SLM) (LC-R 2500, Holoeye). The excitation light passes through two polarizers, P1 and P2, for intensity adjustments and setting the polarization angle of the incident beam on the SLM. A half-wave plate after the polarizer allows adjustment of the polarization angle without changing the intensity of the laser. The SLM is located between an analyzer and a half-wave plate. With a spatial filter and multi-pixel combination, the phase and amplitude of light reflected from the SLM can be controlled independently. Here we only adjust the phase of the reflected light. To calibrate the SLM input versus phase relationship, a phase shifting interferometer is integrated into the system. The reference mirror is installed on a piezo-actuated nano-positioning stage (17MAX301, Melles Griot) to introduce a precise phase shift. The reference beam and the measurement beam from the SLM are combined by a beam splitter, so when interference takes place, interference fringes are formed. The interference pattern is projected on to a CCD camera by lens L4. The surface of the SLM is conjugate to the front surface of the CCD plane. The phase of the SLM can then be obtained using the Hariharan algorithm and unwrapped by a discrete cosine transformation based on the phase-unwrapping algorithm. The calibration system can both register the location of the pupil and be used for displaying the measured wavefront on the SLM. The calibration system can be switched from the main system by a flipper mirror F1. The modulated beam is focused on the sample through a 60× water immersion objective with a numerical aperture of 1.1 (Olympus Microscope, Center Valley, Pa.). Lenses L3 and L5 image the exit pupil of the objective on to the SLM. The emission light is separated from the excitation light by a dichroic beam splitter DB. After passing through an emission filter, the modulated emission light is finally detected by an electron multiplying CCD (EM-CCD) camera (Cascade II:512, Photometrics) for the optimization of the scattered light field phase. After the optimal input phase is determined, the flipper mirror (F2) is switched up to direct light through a second emission filter (E2) and onto the wavefront sensor, which is composed of a 11×11 element lenslet array (AOA Inc., Cambridge, Mass.), with a lenslet diameter of 400 µm and a focal length of 24 mm and a CCD camera (M1400, Dalsa). The pitch of the lenslet array is 400 µm. The spatial filter SF2 is used to reject scattered and background light. The size of SF2 is chosen based on the highest spatial frequency that was detectable with the wavefront sensor. In an example of the system, a pinhole with diameter of 400 µm is used which corresponds to a minimum spatial period of 800 µm on the aperture of the wavefront sensor. The sample is installed on a nano-positioning stage (NanoMax, Thorlabs) for precise alignment of the bead.

In the system, the pupil on the SLM is divided into 316 square segments, which is conjugate to the exit pupil of the objective. The phase of each segment is modulated independently by the SLM. The emission light from the target is collected by the EMCCD.

The sum of the intensity of 20×20 pixels around the target on the image was calculated as the intensity measurement. The step-wise optimization was performed to retrieve the best phase. For each segment, the phase changes from 0 to $2\pi$ in 5 steps. The best phase is calculated by fitting intensity measurements for these 5 steps with a sinusoid function. The optimal phase for the current segment is updated before advancing to the next segment. Operation time is mainly limited by the response time of the SLM, which is 80 ms in the current setup. The exposure time for EMCCD is set as 20 ms. A full compensation takes 158 s. Longer operation times will expose the sample to potential photobleaching and photo-damage. For live samples, the extended operation time also causes the loss of IF because of the dynamic change of optical properties and the drift of the stage. By using fast modulators, such as a DMD or a segmented MEMS deformable mirror, more segments can be used in a shorter amount of time. Because the intensity gain is proportional to the number of the segments, fast modulators will dramatically improve the performance for imaging of live samples.

IF of Light onto Guide-stars

Most of the wavefront correction methods used in microscopy are based on probing either fluorescent or backscattered light from the sample for wavefront measurement using a wavefront sensor and a guide-star or indirect phase optimization. However attenuation of the excitation light caused by scattering will decrease the SNR and degrade the system performance. Increasing the laser power will lead to photobleaching and photo-damage of the sample and further increase background noise. A promising solution to overcome these issues is IF of concentrated light onto guide-stars for wavefront measurements, such as a fluorescent microsphere or protein. Focusing light through scattering tissue can be achieved when light interferes constructively at the target. Only one guide-star inside of the scattering tissue needs to be illuminated for each wavefront measurement. By using fast light modulators, such as the Digital Micromirror Device (DMD) from Texas Instruments, the total operation time can be less than one second, which is acceptable for most of imaging situations.

To quantify the system performance, the excitation distribution on the guide-star can be calculated as:

$$I_{GS}(x,y) = |h_{psf}(x,y)|^2 f_{flou}(x,y) \quad (1)$$

where $h_{psf}$ the PSF at the plane. $f_{flou}$ is the fluorophore distribution at the focal plane. Here we neglect fluorescence from out of focus planes by assuming that it can be blocked by the spatial filter (SF2) (FIG. 1). $f_{flou}$ can be simplified as a circular function where a microsphere with a radius of $r_b$ is used as guide-star, giving:

$$f_{flou}(x,y) = \begin{cases} \alpha & \text{for } \sqrt{x^2+y^2} \leq r_b \\ 0 & \text{otherwise} \end{cases} \quad (2)$$

where $\alpha$ is a scaling factor. The PSF is defined as:

$$h(x_2, y_2) = \quad (3)$$
$$\frac{i}{\lambda} \int\int_{\Sigma} P(x_1, y_1) \exp[-ik\phi(x_1, y_1)] \frac{\exp[-ik(r-R)]}{Rr} \cos(n,r) dS_p$$

where $(x_2, y_2)$ are the coordinates in the focusing plane. $(x_1, y_1)$ are the coordinates in the pupil plane. $P(x_1, y_1)$ and $\phi(x_1, x_2)$ are the light field in amplitude and phase, respectively. k is the wave number. n is the unit normal of the pupil plane. r is the unit vector from $(x_1, y_1)$ to $(x_2, y_2)$. R is the distance from the pupil plane to $(x_2, y_2)$. $dS_p$ is the area element on the pupil plane. $\lambda$ is the wavelength of the illumination light. To take into account the exponential intensity attenuation caused by scattering, the pupil function can be calculated as:

$$P(x, y) = e^{-\left(\frac{z_p}{2L_{se}\cos(n,\vec{r})}\right)} \quad (4)$$

where $z_p$ is the depth of the guide-star. $L_{se}$ is the mean free path (MFP). For simplicity, we assume the pupil is illuminated evenly. Substituting Eq. (4) and Eq. (3) into Eq. (1) leads to the intensity of the guide-star inside of the tissue. Because the wavefront sensor collects the ballistic light from the guide-star, Eq. (4) is only satisfied when scattering of either excitation or emission light is fully compensated. Without any compensation, the square of the pupil function should be used instead.

Figure 2:
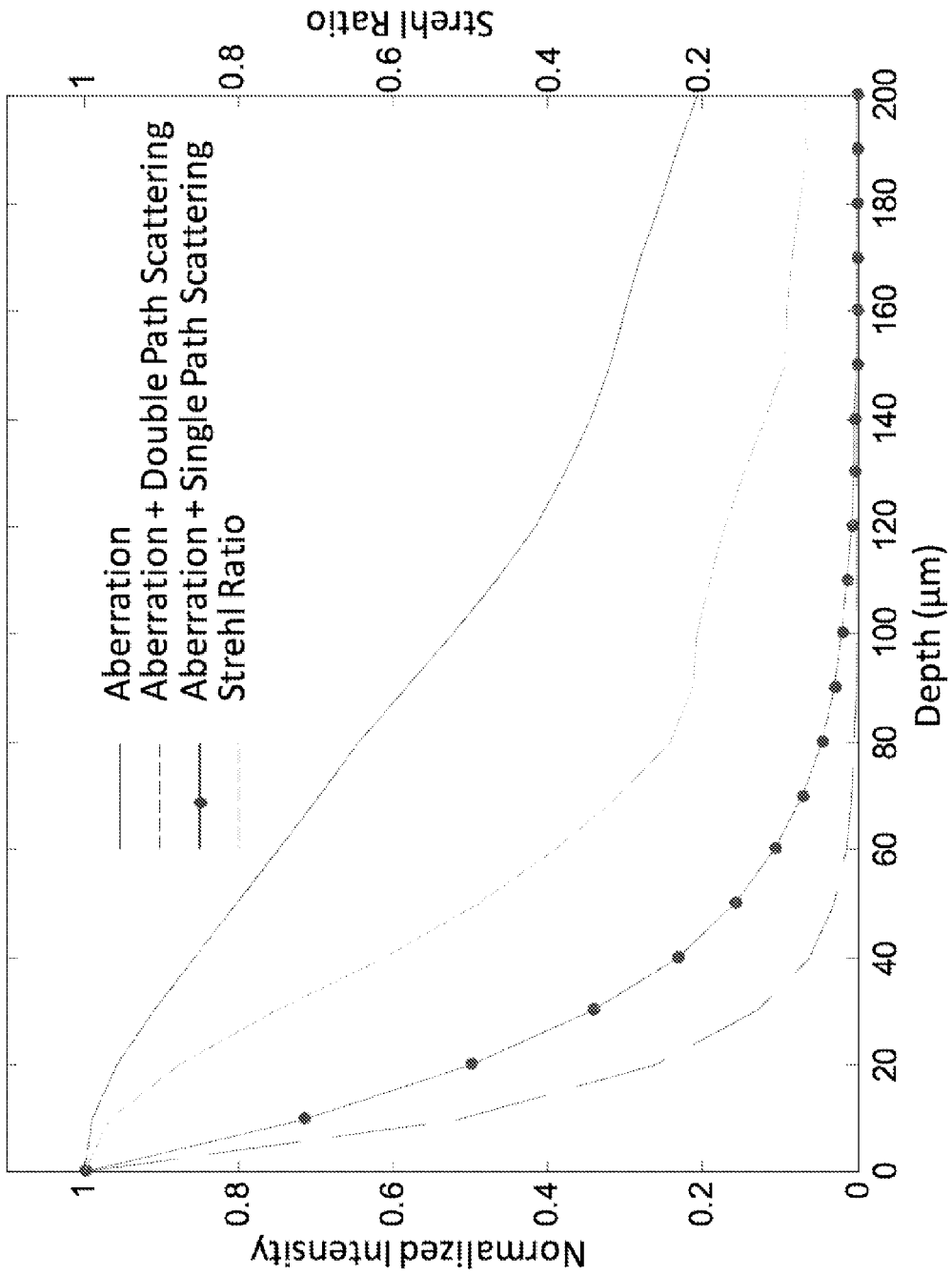
FIG. 2 shows according to an exemplary embodiment of the invention results of modeling the intensity of guide-stars with aberration, aberration and double path scattering, aberration and single path scattering and the Strehl ratio.

Here we use a fluorescent microsphere with a diameter of 1 µm as guide-star. The wavefront, $\phi$, of mouse brain tissue with a thickness of 100 µm is measured using the SH wavefront sensor. In the simulation, we assume the amplitude of the wavefront is proportional to the depth of the tissue. To measure the MFP of the mouse brain tissue, brain slices with thicknesses of 100 µm, 150 µm and 200 µm are prepared. Images of a fluorescent microsphere under the tissue are captured. By using the method described in (van Putten et al., Spatial amplitude and phase modulation using commercial twisted nematic LCDs, Appl. Opt. 47(12), 2076-2081 (2008)), the MFP is measured as 30.82 µm with 95% confidence bounds of 29.12 µm and 32.74 µm. Next the normalized intensity of the guide-star was calculated in three circumstances: when there is only aberration, aberration with single path scattering and aberration with double path scattering, as shown in FIG. 2. As can be seen, the intensity of the guide-star decreases exponentially with the imaging depth. At a depth of 100 µm, the intensity of a guide-star with double path scattering is around 0.1% of the one without scattering. In the case of perfect phase conjugation for compensation of the scattering in excitation light, the intensity of the guide-star can be increased by 5 times at a depth of 50 µm. In the real situation, the improvement by IF is limited by a variety of factors, such as the finite size of the modulator, the limited resolution of the modulated phase and phase only modulation. Because the depth of the guide-star in the sample is within several MFPs, the intensity improvement is moderate compared with the results for more highly scattering samples. Although most of the attenuation is caused by scattering, correction of the aberration alone can increase the intensity by nearly two times and the Strehl ratio, where it is defined by the ratio of peak intensities in the aberrated and ideal PSF, by nearly five times at a depth of 100 µm.

Wavefront Measurement

The emission light from the guide-star was detected by a SHWS with a 11×11 lenslet array. It can make a reliable measurement of an aberration up to the first 97 Zernike modes, which is high enough for correcting refractive aberrations in most biological tissues. Before wavefront measurement, a reference pattern is recorded with collimated light fed into the system. During measurement, the slope of the wavefront on each sub-aperture was calculated by the displacement of the spot on the wavefront sensor. Then the wavefront is reconstructed by the vector-matrix-multiplication (VMM) method. The measurement noise of the wavefront sensor is related to the signal to noise ratio (SNR) of the camera, which can be estimated using:

$$\sigma_m = \sqrt{2}\,\frac{\pi^2 K_g}{4(SNR)}\left[\left(\frac{3}{2}\right)^2 + \left(\frac{\theta d}{\lambda}\right)^2\right] \quad (5)$$

where $K_g$ is a constant to account for centroiding errors due to the fill factor on the CCD, $\theta$ is the angular radius of the spot size, $\lambda$ is the wavelength of the excitation light and d is the sub-aperture diameter. The signal to noise ratio of the detector is given by:

$$SNR = \frac{n_p}{\sqrt{n_p + N_D[n_B^2 + (e/G)^2]}} \quad (6)$$

where $n_p$ is the number of detected photoelectrons per sub-aperture, $N_D$ is the number of detector pixels per sub-aperture. $n_B$ is the number of detected background electrons per pixel, e is the read noise and G is the intensifier gain.

Sample Preparation

Fixed brain slices from a YFP-M line transgenic mouse were prepared. Brain coronal sample sections each at a thickness of 50 µm, 75 µm and 100 µm were cut with a microtome. The samples were kept in Phosphate Buffered Saline (PBS) solution and stored at 4° C. until use. One micrometer diameter crimson fluorescent microspheres (Invitrogen, Carlsbad, Calif.) were deposited onto a glass slide and a cover plate for use as laser guide-stars. Custom-made chambers were made on the glass slides for mounting the thick tissues. Before measurement, the samples were mounted in a chamber with 5% agarose. To avoid changes in the optical properties caused by the evaporation of water from the sample, all the measurements were performed within 10 hours of mounting.

Measurement and Correction of Wavefront Aberration in Mouse Brain Tissues

Because the surface of the SLM is not perfectly flat, it leads to optical aberrations in the system. To compensate this system aberration, the phase induced from the SLM's surface was measured using a phase shifting interferometer, which has been integrated into the system. An opposite phase map, shown in FIG. 3A (bottom), was applied to the SLM to compensate its surface phase. The spherical aberration induced by the cover glass was initially compensated by adjusting a correction collar on the objective lens. To investigate the present method, we performed the wavefront measurement using IF of light onto the guide-star. First, the fluorescent microsphere at the bottom of the mouse brain tissue with a thickness of 100 µm was illuminated by the laser with a wavelength of 633 nm using only the system correction. The image of the microsphere and the phase on the SLM are shown in FIG. 3A (top). The brightest intensity was achieved by precisely adjusting the position of the microsphere in a three dimensional space with respect to the objective using a nano-positioning stage. Then IF was performed to compensate scattering in the sample. A much brighter image was achieved as shown in FIG. 3B (top). The intensity increased two times.

Figures 4A, 4B:
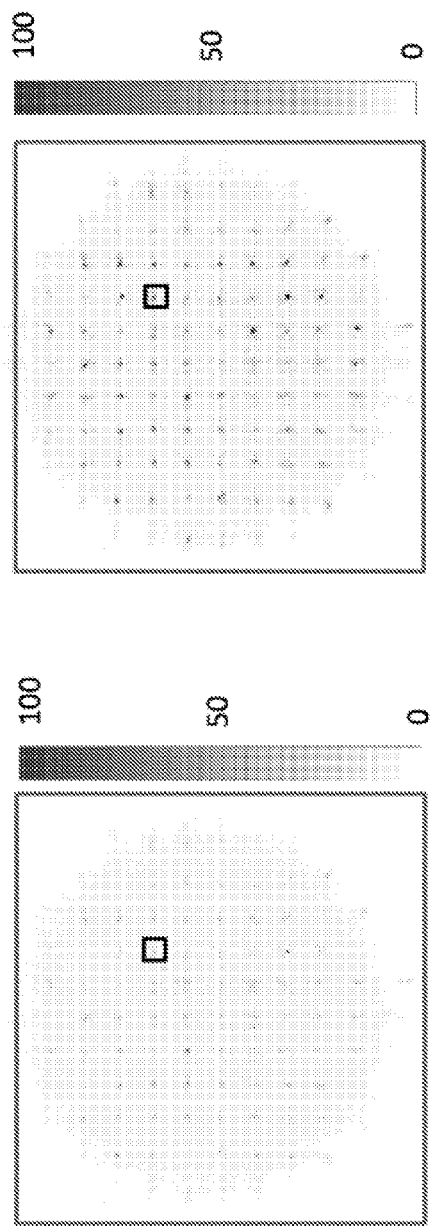
FIGS. 4A-C show according to an exemplary embodiment of the invention wavefront measurement results using IF guide-stars: Complete images from the SH wavefront sensor (grayscale inverted for clarity) and images of a single spot indicated by white square before (FIG. 4A) and after (FIG. 4B) IF.

The images from the wavefront sensor before and after IF are shown in FIGS. 4A-4B, respectively. After IF, the SNR of the wavefront sensor increased from 41.88 to 83.70. The RMS error decreased from 0.22λ to 0.11λ. The intensity of the spots on the wavefront sensor more than doubled. The phase map after IF optimization is shown in FIG. 3B (bottom). The random phase corresponds to the suppression of the scattering effect from the diffuse light. The relatively smooth shape close to the center of the phase map is from wavefront error from ballistic light. FIG. 3C (bottom) shows the wavefront error measured from the wavefront sensor. A similar shape as is seen on the SLM in FIB. 3B (bottom) can be observed on the wavefront error map determined by the SHWS shown in FIG. 3C (bottom). The phase image displayed on the SLM will contain both low-order and high-order corrections. The low-order corrections are expected to extend to a larger isoplanatic patch than the high-order corrections, so we are interested in obtaining the low-order corrections to correct a larger patch. It may be possible to separate out the low-order and high-order aberrations in the SLM instead of using the SHWS to determine the low-order aberration when the refractive aberration is the dominant factor. But when scattering becomes the dominant factor, separating them could be difficult because of the highly random phase for compensation of scattered light. An additional factor is that the light paths taken by photons traveling to the guide-star in IF determined by channel demixing may be different than the light paths taken by ballistic photons that travel along paths determined by least travel time, so the low-order aberrations measured using the SLM and SHWS may be different since they could sample different volumes of the sample.

Figure 4C:
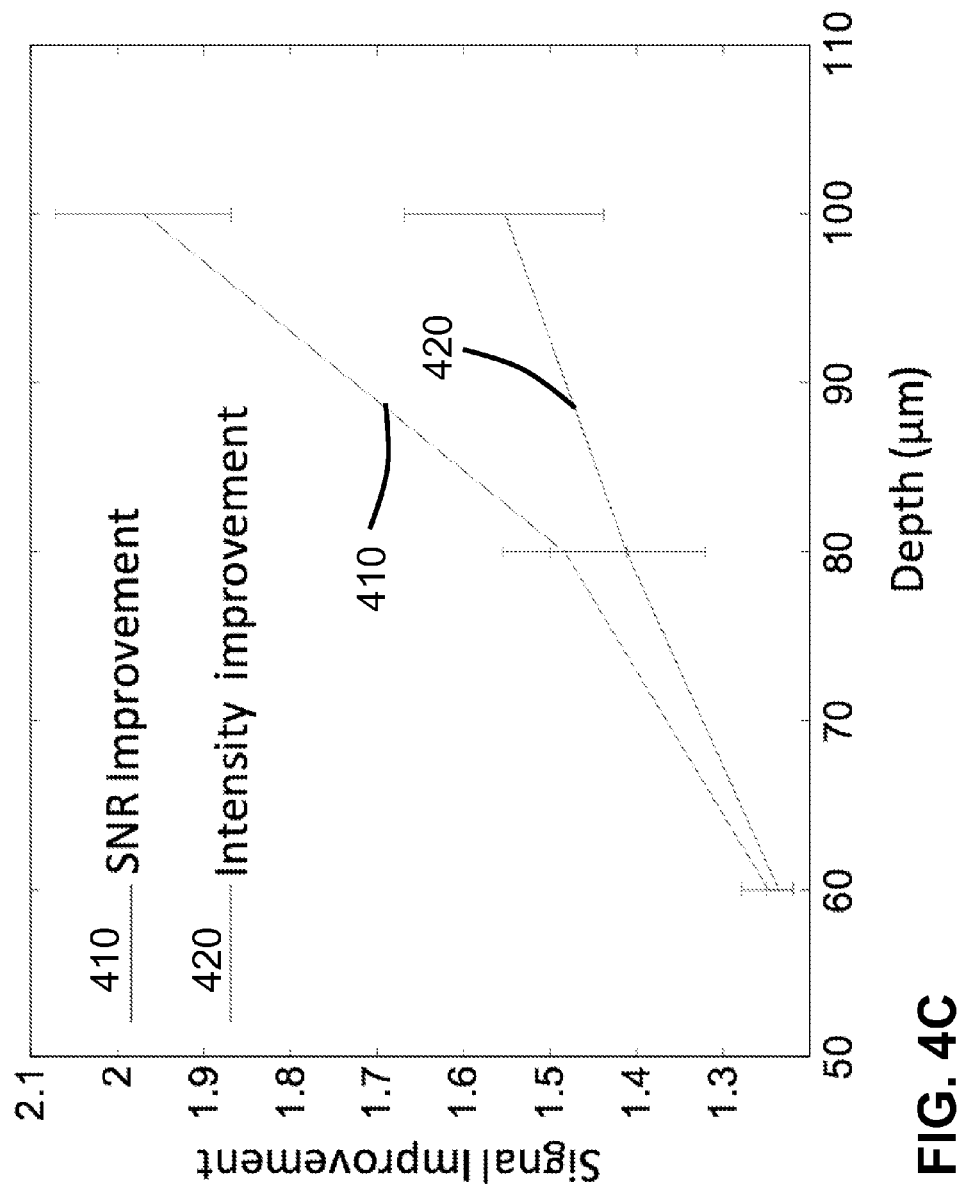

The image of the microsphere after applying this wavefront measurement to the SLM is shown in FIG. 3C (top). The intensity increases 1.5 times compared with the image before wavefront correction in FIG. 3A (top). We also tested the method for fixed brain tissues with variable thicknesses. Three fixed brain tissues were prepared with thicknesses of 60 μm, 80 μm and 100 μm. The SNR improvement of the wavefront sensor and the intensity improvement of the image after wavefront correction are shown in FIG. 4C. As can be seen, the intensity improvement follows a linear trend. The difference between these two improvements is from 0.013 at the image depth of 60 μm to 0.418 at the depth of 100 μm, because scattering effects become a more dominant factor for attenuation of the light for the thicker tissue.

Noise Suppression for Multiple Guide-stars

Figure 5A:
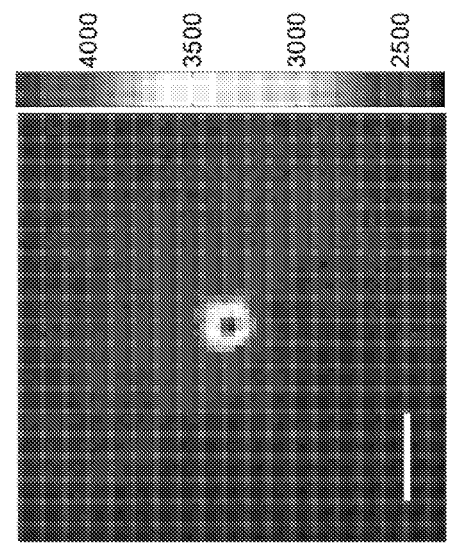
Figure 5B:
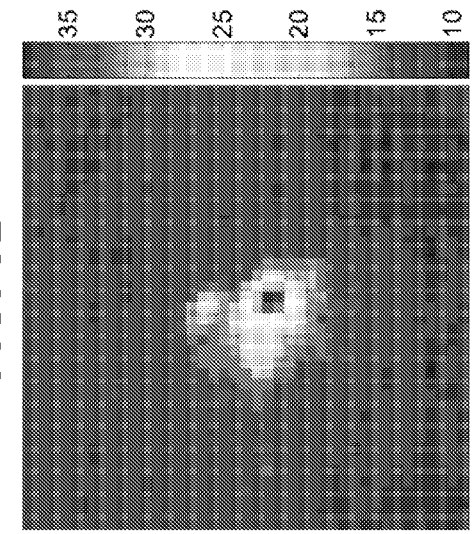
Figure 5C:
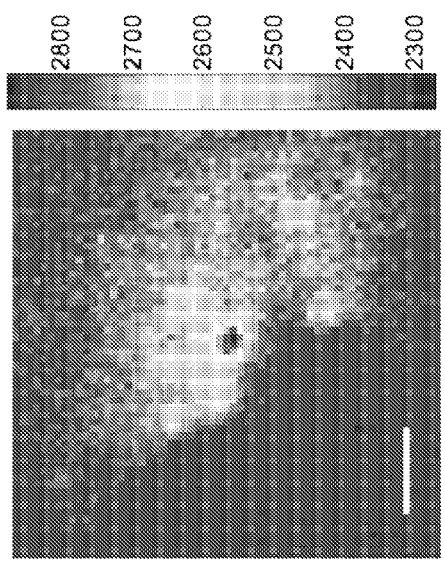
Figure 5D:
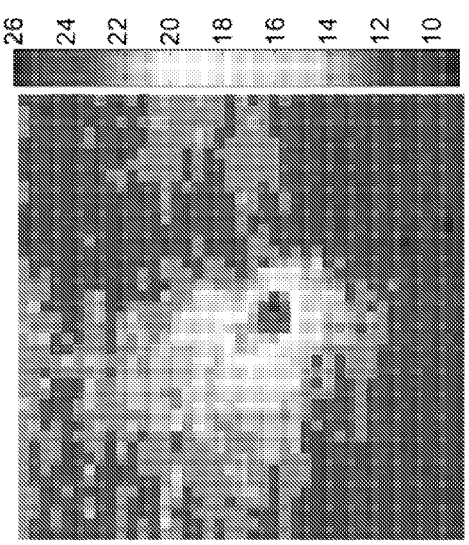

Another advantage of using IF to focus light onto a guide-star is the ability to eliminate the noise from neighboring guide-stars for wavefront measurement. The diffuse part of the excitation light increases the illumination area at the focal plane. If there are multiple guide-stars located inside of this area, the emission from the neighboring guide-stars will increase background noise for wavefront measurement. FIG. 5A shows the image of multiple beads without compensation for scattering. The encircled energy from the center of the bead is calculated as shown in FIG. 5E. The radius of the area containing 80% of energy is 2.67 μm. It generates a significant noise on the wavefront sensor as shown in FIG. 5C. After IF, the focus is much more concentrated as shown in FIG. 5B. 80% of the energy is concentrated in an area with a radius of 1.45 μm. The corresponding image of a spot from the wavefront sensor shows a much brighter spot with less background noise as shown in FIG. 5D.

Section 2

As light passes through biological tissue it can be absorbed, refracted and scattered, limiting the resolution and depth of optical microscopy in biological tissues. Overcoming these challenges will transform the field of non-invasive optical imaging in biology. Many tissues have low absorption within known optical pass bands, leaving refraction and scattering as the dominant imaging challenges. Refraction tends to blur and shift features in the image when imaging through structures or layers with varying indices of refraction, such as the different layers in the mouse brain. It also tends to increase the size of the focal volume, decreasing resolution and fluorescence excitation. Scattering randomizes the trajectory of photons in turbid media and exponentially decreases the intensity of ballistic light with depth into the sample, limiting the imaging depth. To compensate the loss of light, the intensity of the excitation laser can be increased exponentially with imaging depth, but eventually at sufficiently high intensity background fluorescence excited at the surface of the sample becomes as bright as the fluorescent signal at the focal point, so all image contrast is lost. These two effects, the degradation of the optical focus, which limits the signal generation deep inside the tissue, and the background fluorescence near the sample surface, have been said to limit the maximum achievable imaging depth in deep tissue two-photon microscopy.

The invention provides embodiments to overcome both of these limitations using wavefront shaping. Adaptive optics using geometric refocusing can be used in biological imaging to correct for the phase aberrations caused by refraction, enabling diffraction limited imaging through thick tissues. Adaptive optics using interferometric refocusing can also be used to overcome scattering in living tissues. Both effects limit the ability to image deeply in a sample at the diffraction limit.

By combining wavefront shaping for refraction and scattering, we can use the ballistic light more efficiently by decreasing the focal volume to increase resolution and excitation, and use scattered light to increase the intensity of fluorescent light at the focus rather than increasing the intensity of the excitation laser with imaging depth. We have found that we can increase the intensity of fluorescence by 2.5-3× by correcting the refractive phase aberrations, which would enable imaging approximately one additional scattering length deeper into the sample.

Figure 6C:
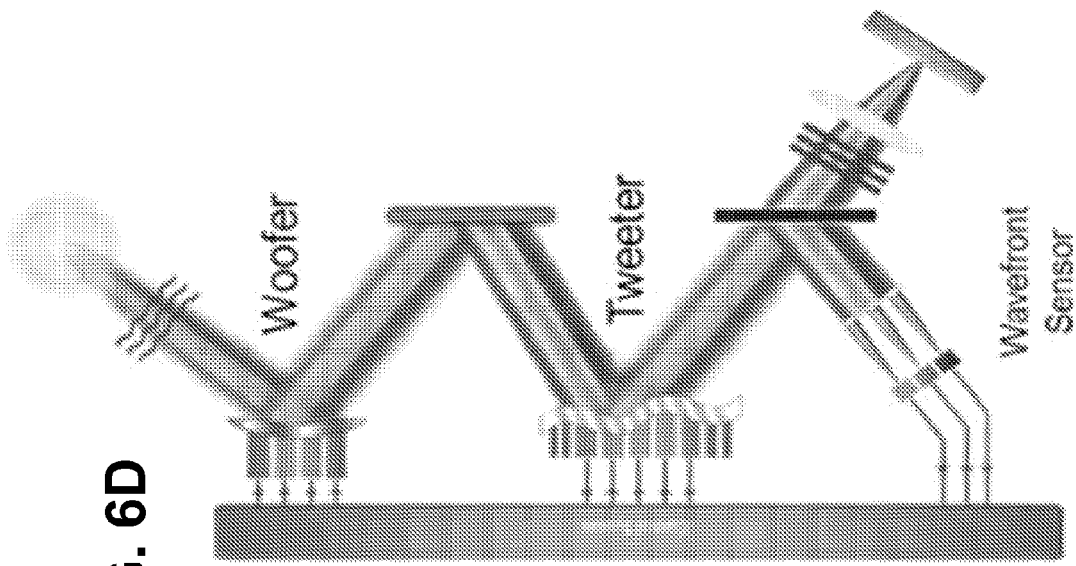
Figure 6D:
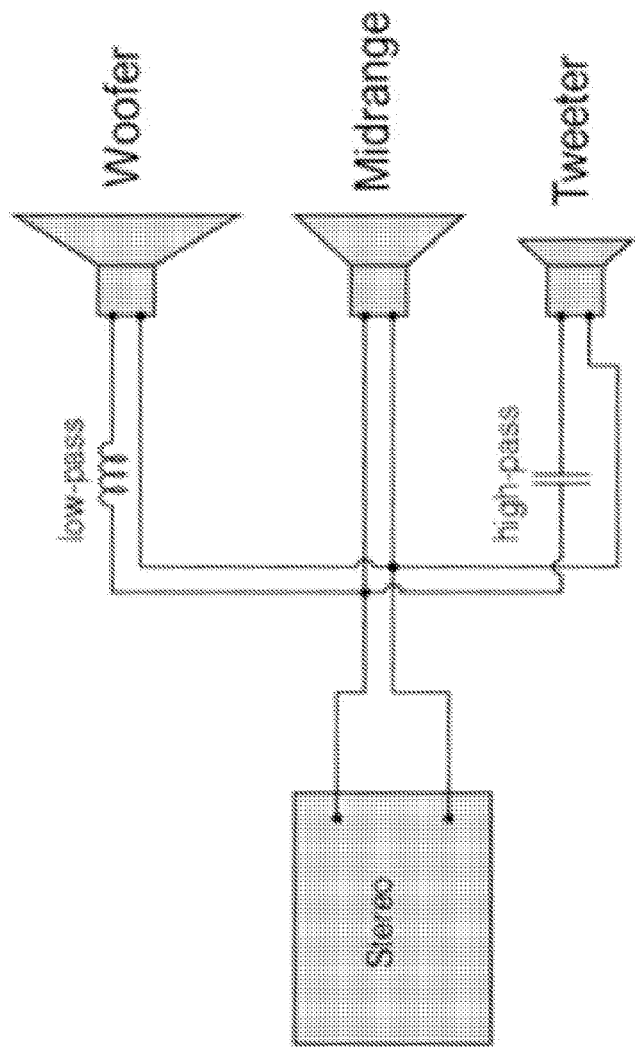

In one embodiment, we correct refractive image aberrations and compensate scattering by combining geometric and interferometric refocusing of light onto guide-stars using a woofer-tweeter wavefront shaping system (FIGS. 6A-D). The woofer, using a deformable mirror, is used to correct low-spatial frequency refractive phase aberrations (FIG. 6A), to tighten the focal spot and correct geometric distortions in the image due to changes in the refractive index. These aberrations are measured using a Shack-Hartmann wavefront sensor. The tweeter, using a spatial light modulator (SLM), is used to compensate high-spatial frequency scattering (FIG. 6B). High-frequency wavefront shaping is used to refocus light that has been scattered, increasing the excitation light focused onto the guide-star.

Refractive Phase Aberrations

Our method for correcting refractive phase aberrations is based on the use of adaptive optics in astronomical imaging. In astronomy a guide-star is used as the reference beacon for making wavefront corrections. If there is a star next to the science object that is to be imaged, that "natural guide-star" can be used to measure the wavefront errors that occur as light travels through Earth's atmosphere. If the natural guide-star is sufficiently close to the science object of interest, it will go through the same part of the atmosphere and acquire the same aberrations. Since it is known that the guide-star is a point of light, any deviations from a point of light can be measured and corrected using an adaptive mirror. By measuring the distortions of the wavefront with a wavefront sensor, the conjugate or opposite shape can be placed on the mirror. When the light is reflected, the wavefront is corrected, and a sharp image of the object is captured by a high-resolution camera. If there is not a natural guide-star near the science object, a "laser guide-star" can be created by projecting a sodium laser beam from the dome of the telescope, which intersects a layer of sodium vapor in the mesosphere at a height of ~100 km, causing it to glow. The fluorescence from the guide-star can be used to make wavefront measurements. In biology there are few natural guide-stars, so we have created laser guide-stars using fluorescent proteins.

Scattering

Figure 7A:
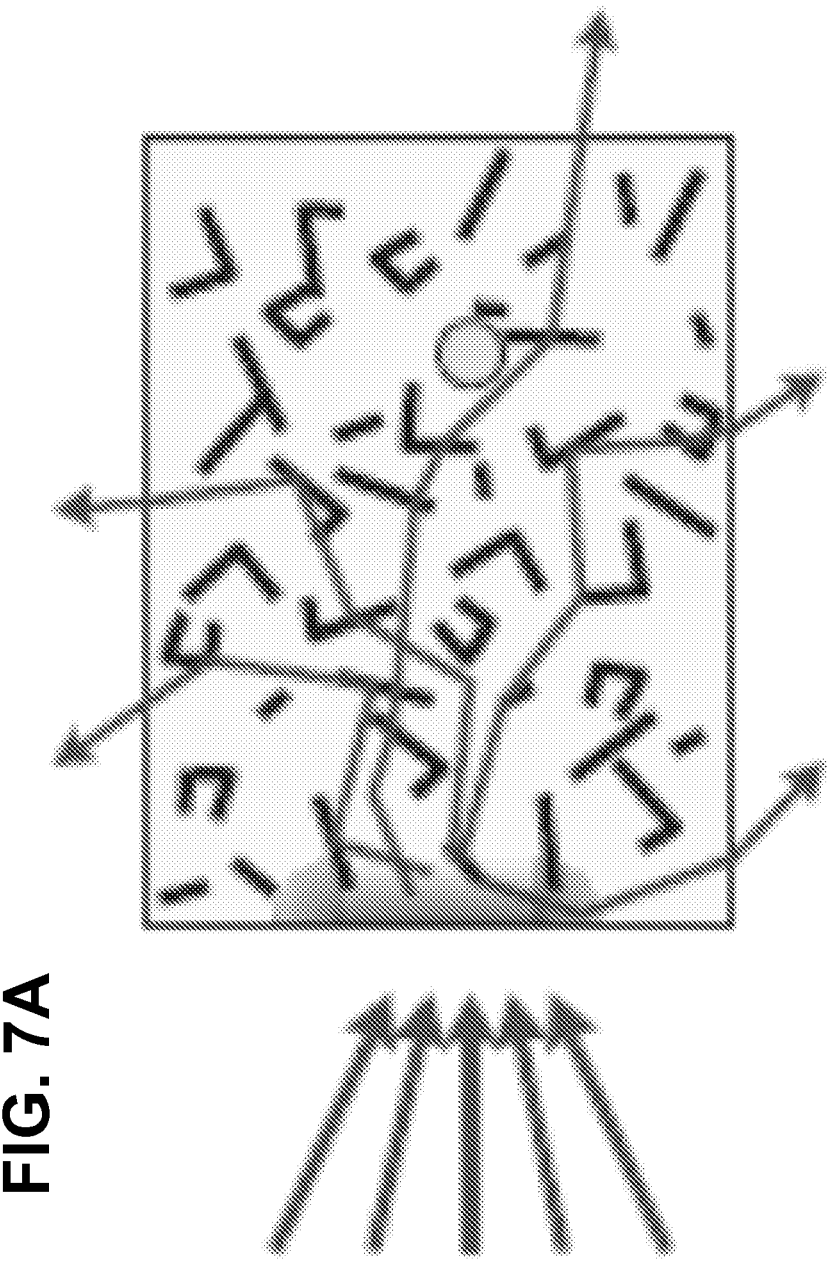
Figure 7C:
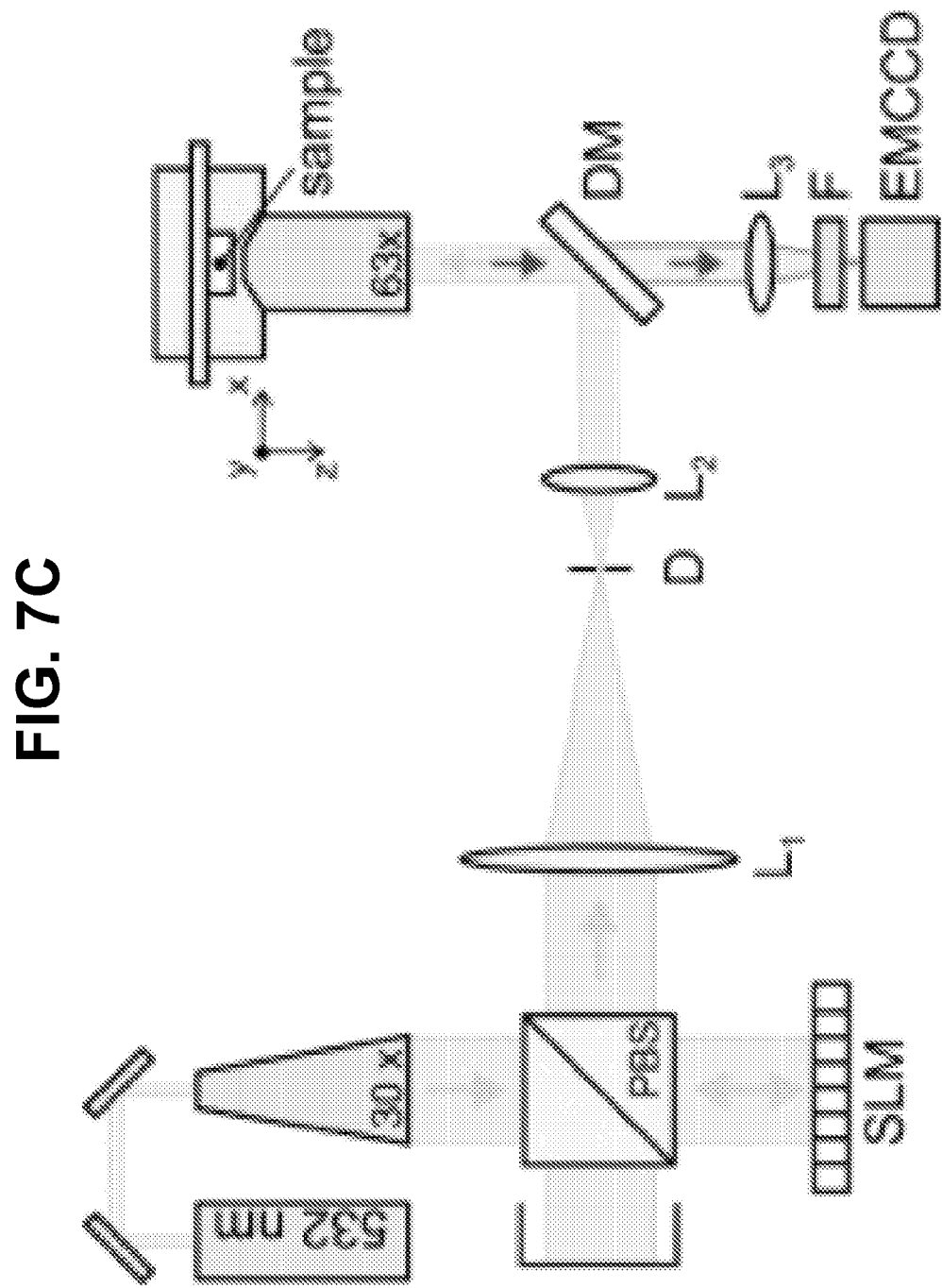

Our method for compensating scattering is based on Coherent Adaptive Optical Techniques (COATS) that were originally developed for refocusing high-power laser light through the atmosphere onto a target. Here a laser is projected onto a target such as a missile or unmanned aerial vehicle (UAV), and a "glint" from the target is used as a guide-star reference beacon to compensate for aberrations such as thermal blooming that is caused by the laser heating the atmosphere. The wavefront is actively shaped by a spatial light modulator (SLM) to increase the intensity of light delivered to the target by maximizing the light returned from the glint. Using feedback from a fluorescent guide-star within a scattering sample, we have used the method to refocus light onto a guide-star through scattering tissue (FIG. 7A-C). In FIG. 7A, light is focused into scattering medium using geometric optics (i.e. a lens). In FIG. 7B, the wavefront is refocused using wavefront shaping to form an interferometric focus at the guide-star (710). The wavefront is shaped using the SLM as shown in the optical set-up shown in FIG. 7C. A 532 nm laser is expanded and illuminates a liquid crystal Spatial Light Modulator (SLM) that spatially modulates the phase of the reflected light. The SLM is imaged onto the back aperture of a 63X microscope objective that focuses the modulated light into a sample. Fluorescent light is collected by the same objective and imaged with an electron multiplied (EM) CCD camera. A computer (not shown) controls the SLM based on the EMCCD images. To ensure that light is interferometrically refocused onto the guide-star at the focal point of the objective lens, we used a modification of focal modulation microscopy (described infra). We also used a high-speed, high-order spatial light modulator to quickly (~50 ms) obtain an intense (~20× gain) interferometric refocus.

The objective of this invention is the application of the combination geometric and interferometric refocusing of long wavelength light ($\lambda$=1,300-1,700 nm) through scattering mouse brain tissue onto "brainbow" labeled neurons in different brain layers. By using both refractive and interferometric refocusing we can correct for refractive phase aberrations and shape the wavefront for "un-scattering" separately. This method has the following advantages. First, interferometric refocusing can be used to illuminate the guide-star that is used for correcting phase aberrations. This allows imaging faster and more deeply through turbid media (described infra). Second, since the refractive phase aberrations are more slowly varying across a region of tissue than scattering related losses, correction of phase aberrations at one point improves imaging at all other areas within the isoplanatic region. We call this region an "R-patch", for the isoplanatic region that has been corrected for refractive image aberrations. Thus one correction in the center of an R-patch will help correct refractive phase aberrations over an extended region, ~38 μm in diameter.

In contrast, wavefront shaping to compensate for scattering results in a compensated region that is much smaller in extent, approximately 10 μm in diameter. We call this region an "S-patch", for the region that has been compensated for scattering. The R-patch has an area that is ~14 times larger than the S-patch. The requirement for making corrections at each S-patch for both refraction and scattering pushes the limits of spatial light modulators (SLM) and their optimization strategies. By first correcting phase aberrations within an R-patch we reduce the optimization time for obtaining an interferometric refocus since we only need to compensate for scattering within each S-patch. This allows for faster imaging with less photo-bleaching. Correcting refractive aberrations also removes geometric image distortions that are not removed through optimization for un-scattering (described infra).

Wavefront Shaping

Wavefront shaping requires a guide-star as a reference beacon. Wavelength ($\lambda$=1,300-1,700 nm) ballistic light is used to selectively illuminate a single guide-star sufficiently brightly to allow interferometric refocusing deep within a scattering specimen with the objective to reach a depth of ~2,000 μm to enable imaging throughout the for example an entire mouse hippocampus. In one embodiment, an optical parametric oscillator ($\lambda$=1,000-1,600 nm and 1,750-4,000 nm) is added to a femtosecond laser ($\lambda$=680-1080 nm) to extend our excitation wavelength range into the near IR, which has less scattering in tissue (~$1/\lambda^4$). The guide-star is then used for making wavefront measurements and corrections deep in the sample. In an alternative embodiment, we can also use a regenerative amplifier to further increase the excitation efficiency by lowering the pulse repetition frequency.

We have used interferometric refocusing of visible light to illuminate a guide-star for making measurements of refractive phase aberrations. We more than doubled the signal to noise ratio of the laser guide-star through scattering tissue. While we have only increased the intensity by 2.7×, this result was limited by the slow liquid crystal spatial light modulator that we used (70 Hz frame rate), and the limited number of degrees of freedom—we could optimize due to this slow update rate. In another example, we use a fast spatial light modulator (34 kHz frame rate) with a large number of degrees of freedom (1020 actuators), which could enable an interferometric refocus with an intensity gain of ~20×.

Geometric and Interferometric Focusing

Figure 8:
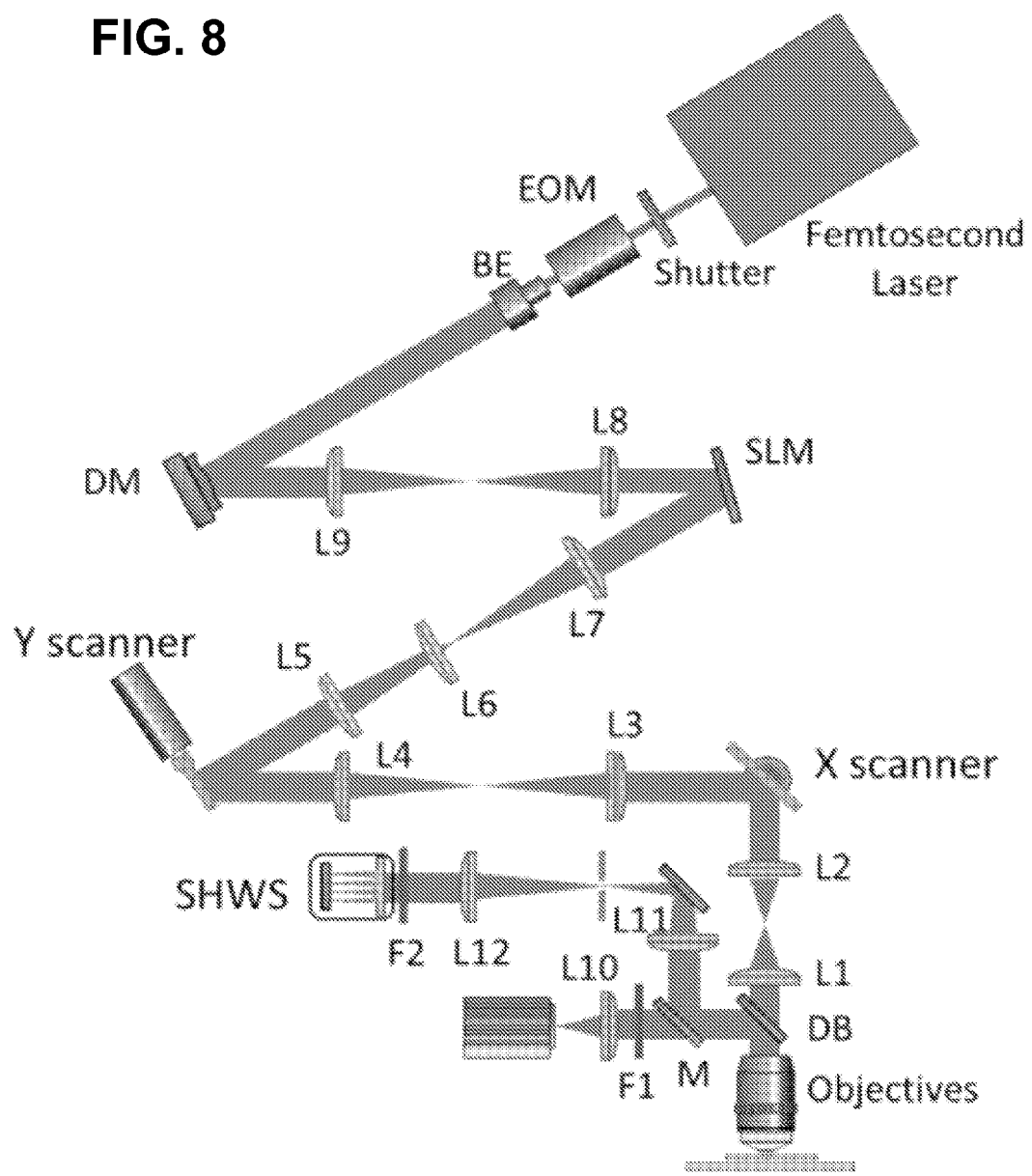
FIG. 8 shows according to an exemplary embodiment of the invention an integration of the interferometric refocusing subsystem into our AO two-photon microscope. L: Lens, F: Filter, P: Polarizer, M: Mirror Flipper, DM: Deformable Mirror, DB: Dichroic Beamsplitters, BE: Beam Expander, SLM: Spatial Light Modulator, EOM: Electro-optic Modulator. SHWS: Shack-Hartmann Wavefront Sensor. The "woofer-tweeter" subsystem includes the DM and the SLM, which are coupled by the relay optics L8 and L9.

With the combination of the two approaches (geometric and interferometric refocusing) we are able to deep-tissue diffraction limited scanned laser imaging deep in scattering tissue. A fast (34 kHz frame rate) high-order (952 actuators) high-spatial frequency (300 μm pitch) spatial light modulator (SLM) for the compensation of scattered light can be combined with low-spatial frequency wavefront shaping using a continuous face sheet deformable mirror (140 actuators, 2 μm stroke) to correct tissue induced wavefront aberrations in a "woofer-tweeter" combination. Since the spatial extent of the corrected "isoplanatic" R-patch is larger for refractive aberrations (~38 μm in diameter), we can make that correction first, and then compensate smaller S-patches (~10 μm in diameter) for scattering within that area. In one example, we have modeled the addition of a woofer-tweeter wavefront shaping system integrated into our custom built two-photon microscope (FIG. 8). In our results, we found that using the combined approach we more than doubled the signal to noise ratio of the laser guide-star through scattering tissue.

Guide-stars

Fluorescently labeled neurons can be used as guide-stars and structural labels with variable depth and density. The depth and density can be controlled by the population of fluorescent neurons that are excited at a given wavelength, for deep-tissue, multiphoton (2&3 photon) imaging. In one example, different wavelengths of excitation light can be used to illuminate different populations of neurons at different depths. A guide-star searching algorithm can be used to seek out guide-stars based on different search criteria (e.g. brightness, spacing, depth).

Figure 9:
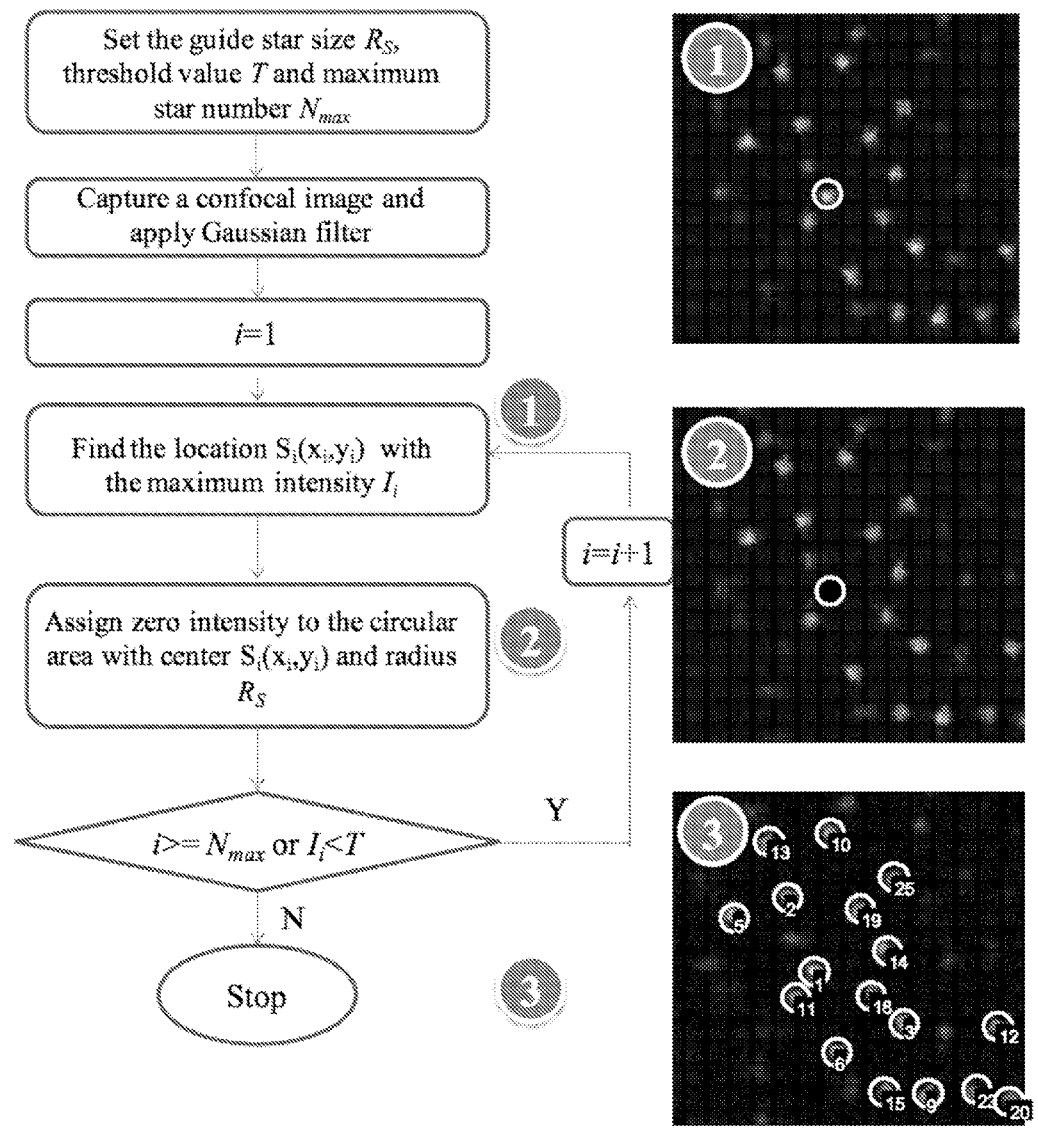
FIG. 9 shows according to an exemplary embodiment of the invention a flowchart for the guide-star searching algorithm using confocal microscopy.

To image several S-patches (~10 μm) within a larger R-patch (~38 μm) the algorithm localizes the desired guide-star automatically during the imaging process (FIG. 9). The algorithm first initializes the guide-star size $R_s$, the threshold value T for image thresh-holding and the maximum star number $N_{max}$. The number of guide-stars that are detected depends on these settings. The noise in the image is first removed using Gaussian filters. The location $S_{max}$ of the global maximum of the image is achieved, which is the first guide-star. This guide-star can be used for correcting an R-patch, which will correct the entire area within the ~38 μm isoplanatic area, including several ~10 μm S-patches than can then be compensated for scattering. Since refraction has been corrected the geometric relationship between these S-patches can be determined. This is not the case if a refractive correction is not made first. The next guide-star can be located by assigning zero to the area of the previous guide-star and searching for the maximum of the modified image.

Focal Modulation

Focal modulation can be used in some embodiments to ensure that the geometric focus and the interferometric focus are coincident. This is especially important to consider when the interferometric focusing optimization algorithm optimized on a guide-star was not at the focal point for ballistic photons. A modification of focal modulation microscopy is one example to ensure that the guide-star at the focal point is chosen. In focal modulation microscopy a phase modulation can be added onto the excitation path in a confocal microscope that induced an intensity modulation mainly in the focal volume, which was detected and amplified using lock-in techniques. This enables suppression of background fluorescence from scattering since only the ballistic photons have well defined phase and contribute to the modulated signal.

The extension of this technique for two-photon focal modulation microscopy was found to increase the SBR by 30 dB at a depth of 1,600 μm, increasing the potential imaging depth from 5-61 s to 81 s. In embodiments of this invention, we modulate the focus in our two-photon microscope by adding a small sinusoidally varying phase aberration (f=5 kHz, T=0.2 ms) on to our deformable mirror, which will mostly modulate the ballistic focal volume. Since our pixel integration time for interferometric focusing will be ~50 ms, we will average over ~250 cycles of this AC dither signal and thus the aberration will not impact our focal spot size, which will be determined by the static (DC) shape of the deformable mirror.

A phase aberration has previously been used for PSF shaping in three-dimensional super-resolution microscopy to improve axial resolution by applying an adjustable component of astigmatism to a deformable mirror. By using the synchronous amplified signal from the sinusoidal phase modulation for the optimization process to obtain an interferometric refocus, the guide-star at the focal spot for ballistic light can be selected for optimization. A related approach used differential aberration imaging (e.g. the subtraction of two images) to reject background fluorescence in two-photon microscopy. Here we could use lock-in techniques for focal aberration modulation to reject background guide-stars that are located away from the ballistic focal position.

Another aspect relevant to consider is geometric shifts in case the beam is not parked over the brightest spot when they perform their optimization. In one embodiment, one could use focal modulation to obtain an interferometric refocus at the ballistic focal point of the objective lens, which will eliminate these shifts.

In one aspect of the invention, we have demonstrated the ability to illuminate single guide-stars without introducing significant background using non-interferometric focusing of light. This was accomplished by using confocal imaging of the guide-star, so that only the guide-star at the focal point was detected. In another aspect, we have found that interferometric refocusing (IF) preferentially selects the brightest guide-star within the field. To ensure that the interferometric focus is optimized on the guide-star that is at the ballistic focus, focal aberration modulation can be used as feedback for the optimization of the interferometric refocusing. While there may be a crowded field of guide-stars, only the guide-star at the focus for ballistic photons will be "twinkling" (i.e. modulated by the small sinusoidal phase aberration from the deformable mirror), and we then optimize that synchronous signal to obtain an interferometric refocus at the focus for the ballistic light.

What is claimed is:

1. An optical microscopy method for noninvasive imaging of a biological tissue, comprising:
   wavefront shaping using interferometric focusing to compensate for light scattering, wherein the interferometric focusing focuses light onto a guide-star in a biological tissue to illuminate the guide-star, wherein the guide-star is used for refractive and interferometric refocusing of the scattered light in the biologic tissue to correct for refractive phase aberrations and to shape the wavefront for un-scattering the scattered light inside the biological tissue;
   measuring fluorescence from the illuminated guide-star using direct wavefront sensing;
   wavefront shaping using geometric focusing based on the measured fluorescence from the guide-star to correct for refractive aberrations; and
   applying the combined interferometric and geometric wavefront shaping in the optical microscopy method.

2. The method as set forth in claim 1, further comprising selecting the guide-star from a plurality of guide-stars.

3. The method as set forth in claim 1, further comprising using focal modulation to ensure that the interferometric focus at the guide-star coincides with the geometric focus.

4. An optical microscopy method for noninvasive imaging of a biological tissue, comprising:
   wavefront shaping using interferometric focusing to compensate for light scattering, wherein the interferometric focusing focuses light onto a guide-star in a biological tissue to illuminate the guide-star and wherein focal modulation of the ballistic focus is used as an optimization signal for the intereferometric focusing by measuring fluorescence from the illuminated guide-star; and
   using a lock-in method to detect a synchronous signal from the measured fluorescence, wherein the synchronous signal is maximized for obtaining an interferometric refocus, wherein the illuminated guide-star at the focal spot for ballistic light is selected for optimization.

5. The method as set forth in claim 4, further comprising selecting the guide-star from a plurality of guide-stars.

* * * * *